United States Patent [19]

Koyama et al.

[11] Patent Number: 4,757,071

[45] Date of Patent: Jul. 12, 1988

[54] 1,4-DIHYDROPYRIDINE DERIVATIVES, AND PHARMACEUTICAL COMPOSITIONS CONTAINING SAME, USEFUL FOR TREATING CARDIOVASCULAR DISEASES

[75] Inventors: Hiroyasu Koyama, Ageo; Yoshikuni Suzuki, Ohmiya; Koichiro Hagihara, Itami, all of Japan

[73] Assignee: Nisshin Flour Milling Co., Ltd., Tokyo, Japan

[21] Appl. No.: 806,454

[22] Filed: Dec. 9, 1985

[30] Foreign Application Priority Data

| Dec. 14, 1984 | [JP] | Japan | 59-262942 |
| Oct. 21, 1985 | [JP] | Japan | 60-233349 |
| Oct. 21, 1985 | [JP] | Japan | 60-233350 |
| Dec. 2, 1985 | [JP] | Japan | 60-269302 |

[51] Int. Cl.$^4$ .................. C07D 401/12; C07D 407/12; C07D 409/12; A61K 31/455

[52] U.S. Cl. .................. 514/247; 514/255; 514/269; 514/274; 514/309; 514/312; 514/335; 514/336; 514/342; 544/238; 544/333; 544/405; 546/147; 546/170; 546/263; 546/283; 546/284

[58] Field of Search .............. 546/147, 170, 263, 268, 546/275, 278, 280, 281, 283, 284; 544/124, 238, 333, 405; 514/255, 269, 274, 247, 309, 312, 335, 336, 342

[56] References Cited

U.S. PATENT DOCUMENTS

| 3,574,843 | 4/1971 | Bossert et al. | 514/356 |
| 3,799,934 | 3/1974 | Meyer et al. | 546/257 |
| 4,044,141 | 8/1977 | Bossert et al. | 514/150 |
| 4,239,893 | 12/1980 | Pigerol et al. | 546/321 |
| 4,258,042 | 3/1981 | Loev et al. | 514/227 |
| 4,264,611 | 4/1981 | Berntsson | 514/356 |
| 4,317,768 | 3/1982 | Pigerol et al. | 524/99 |

FOREIGN PATENT DOCUMENTS

2182983 12/1973 France .................. 544/238

*Primary Examiner*—Alan L. Rotman
*Attorney, Agent, or Firm*—Cushman, Darby & Cushman

[57] ABSTRACT

2,6-Dimethyl-4-(2- or 3-substituted phenyl)-1,4-dihydropyridine-3,5-dicarboxylic acid diesters, having vasodilating and blood pressure lowering effects, in the ester moiety at the 3-position of which a heterocyclic group is linked to an alkylene group through an ester bond (carbonyloxy group). The diesters are used for treatment of cardiac diseases, cerebrovascular diseases and hypertension.

13 Claims, No Drawings

1,4-DIHYDROPYRIDINE DERIVATIVES, AND PHARMACEUTICAL COMPOSITIONS CONTAINING SAME, USEFUL FOR TREATING CARDIOVASCULAR DISEASES

FIELD OF THE INVENTION

The present invention relates to new compounds having valuable vasodilating and blood pressure lowering effects, etc., to processes for their preparation and to their use as vasodilating and antihypertensive agents.

BACKGROUND OF THE INVENTION 1,4-Dihydro-2,6-dimethyl-4-phenylpyridine-3,5-dicarboxylic acid diethyl ester is known to obtain by reacting 2-benzylideneacetoacetic acid ethyl ester, β-aminocrotonic acid ethyl ester or acetoacetic acid ethyl ester and ammonia, as reported in Ber. Deutsch Chem. Ges. 31, 743(1971). DOS Nos. 2117517 and 2117573 disclose that similar compounds can be used as coronary arteriodilating and antihypertensive agents, and inter alia 1,4-dihydro-2,6-dimethyl-4-(2-nitrophenyl)-pyridine-3,5-dicarboxylic acid dimethyl ester disclosed therein has been used extensively under the name of Nifedipine. Since commercial success of Nifedipine, a large number of compounds having similar chemical structure have been developed and these compounds are disclosed in U.S. Pat. Nos. 3,574,843; 4,264,611; 3,799,934; 4,239,893; 4,317,768; 4,044,141 and 4,258,042; EPO Appln. No. 0012180; and French Patent No. 2,182,983. Further, there are reported in No. WO 84/02132 the compounds wherein a heterocyclic group is linked to an alkylene group through an amide bond in an ester moiety at the 3-position of 1,4-dihydro-2,6-dimethyl-4-phenyl pyridine-3,5-dicarboxylic acid diesters. Known 1,4-dihydropyridine derivatives including Nifedipine inhibit calcium influx into the cells and they have been used as remedy for cardiac diseases of angina pectoris, etc., cerebrovascular diseases of cerebral infarction, etc., and hypertension.

However, it has been reported that these derivatives have the disadvantages such as short-lasting activity and tachycardia.

The present invention results from efforts to develop new compounds with more improved pharmacological effects and lesser side effects than known 1,4-dihydropyridine derivatives.

DISCLOSURE OF THE INVENTION

According to the present invention, there are provided compounds of the formula I

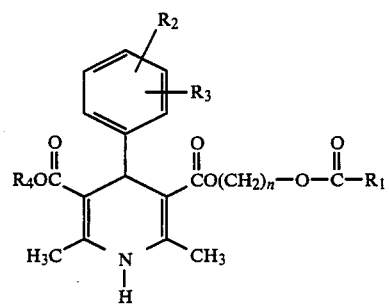

(I)

wherein $R_1$ represents a 5- or 6-membered heterocyclic group having in the ring one or two hetero atoms selected from nitrogen, oxygen and sulfur atoms, said heterocyclic group may be substituted with halogen atom, haloalkyl, amino, acylamino, lower alkoxy, aryloxy, lower alkoxycarbonyl or lower alkyl, and said heterocyclic group may be fused with a carbocyclic ring which may be substituted with lower alkyl or lower alkoxy; $R_2$ and $R_3$ both represent halogen atoms, or one of $R_2$ and $R_3$ represents a nitro or trifluoromethyl group and the other represents a hydrogen atom; $R_4$ represents a straight- or branched-chain alkyl or alkoxyalkyl group, and n represents 2 or 3, and the pharmaceutically acceptable acid addition salts thereof.

By the term "pharmaceutically acceptable acid addition salt" is meant a salt, the anion of which is relatively innocuous to the animal organism when used in therapeutic doses, so that the beneficial properties of the cation are not vitiated by side-effects ascribable to the anion.

In the present specification, wherever reference is made to compounds of formula I, it is intended to refer also to the said acid addition salts, where the context so permits.

In an embodiment of the present invention, the compounds of the formula I wherein one of $R_2$ and $R_3$ represents a nitro group and the other represents a hydrogen atom are of the following formula:

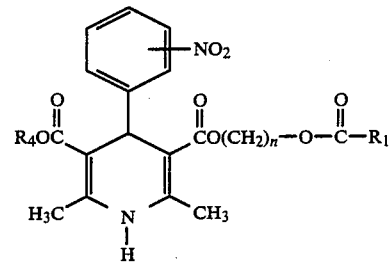

wherein $R_1$, $R_4$ and n are as defined above. In another embodiment, the compounds of the formula I wherein one of $R_2$ and $R_3$ represents a trifluoromethyl and the other represents a hydrogen atom are of the following formula:

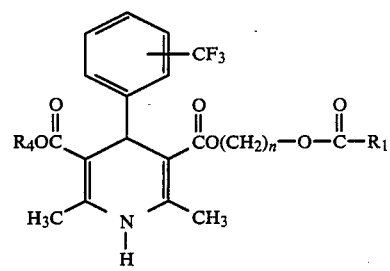

wherein $R_1$, $R_4$ and n are as defined above. In further embodiment, the compounds of the formula I wherein $R_2$ and $R_3$ both represent halogen atom are of the following formula:

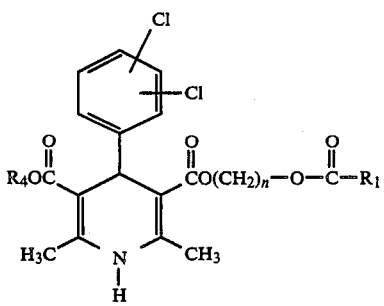

wherein R₁, R₄ and n are as defined above.

As is evident from the above formula I, the compounds of the present invention are those wherein $R_1$ is linked to an alkylene group through an ester bond (carbonyloxy group), which are different from the compounds wherein the heterocyclic group is linked to an alkylene group through an amide bond in an ester moiety at 3-position of 1,4-dihydro-2,6-dimethyl-4-phenylpyridine-3,5-dicarboxylic acid diesters as disclosed in the above-cited prior art No. WO 84/02132. The compounds of the present invention are characterized by marked pharmacological effects as compared with the prior art compounds.

Examples of the heterocyclic groups represented by $R_1$ include 2-furyl, 3-furyl, 2-thienyl, 3-thienyl, 2-pyrrolyl, 3-pyrrolyl, 2-pyranyl, 3-pyranyl, 4-pyranyl, 2-pyridyl, 3-pyridyl, 4-pyridyl, 3-isooxazolyl, 4-isooxazolyl, 5-isooxazolyl, 3-isothiazolyl, 4-isothiazolyl, 5-isothiazolyl, 2-imidazolyl, 4-imidazolyl, 2-morpholinyl, 3-morpholinyl, 2-pyrimidinyl, 4-pyrimidinyl, 5-pyrimidinyl, 2-pyrazinyl, 3-pyridazinyl and 4-pyridazinyl, and the like.

Substituents for such heterocyclic groups include fluorine, chlorine, bromine, iodine, trichloromethyl, trifluoromethyl, amino, acetylamino, benzoylamino, methoxy, ethoxy, propoxy, phenoxy, methoxycarbonyl, ethoxycarbonyl, methyl, ethyl, n-propyl, i-propyl, n-butyl, i-butyl and tert-butyl, and the like. One or more such substituents are substituted on the carbon atom of the above heterocyclic groups.

Examples of the groups formed by fusion of the heterocyclic groups with a carbocyclic ring include 2-quinolyl, 3-quinolyl, 4-quinolyl, 1-isoquinolyl, 3-isoquinolyl, 4-isoquinolyl, 2-quinazolinyl, 4-quinazolinyl and quinoxalinyl and the like. Examples of substituents on the carbocyclic ring of these groups include methyl, ethyl, n-propyl, i-propyl, n-butyl, i-butyl, tert-butyl, methoxy, ethoxy and propoxy and the like.

Groups represented by $R_4$ of the above formula I include methyl, ethyl, n-propyl, i-propyl, n-butyl, i-butyl, sec-butyl, tert-butyl, methoxyethyl, ethoxyethyl ethoxyethoxymethyl and the like.

Examples of preferred compounds are recited below.
(1) 2,6-dimethyl-4-(2-nitrophenyl)-1,4-dihydropyridine-3,5-dicarboxylic acid 3-(2-nicotinoyloxyethyl)ester-5-methyl ester;
(2) 2,6,-dimethyl-4-(3-nitrophenyl)-1,4-dihydropyridine-3,5-dicarboxylic acid 3-(2-nicotinoyloxyethyl)ester-5-methyl ester;
(3) 2,6-dimethyl-4-(3-nitrophenyl)-1,4-dihydropyridine-3,5-dicarboxylic acid 3-(2-picolinoyloxyethyl)ester-5-methyl ester;
(4) 2,6-dimethyl-4-(3-nitrophenyl)-1,4-dihydropyridine-3,5-dicarboxylic acid 3-(2-isonicotinoyloxyethyl)ester-5-methyl ester;
(5) 2,6-dimethyl-4-(3-nitrophenyl)-1,4-dihydropyridine-3,5-dicarboxylic acid 3-[2-(2-chloronicotinoyloxy)ethyl]ester-5-methyl ester;
(6) 2,6-dimethyl-4-(3-nitrophenyl)-1,4-dihydropyridine-3,5-dicarboxylic acid 3-(2-pyrazinoyloxyethyl)ester-5-methyl ester;
(7) 2,6-dimethyl-4-(3-nitrophenyl)-1,4-dihydropyridine-3,5-dicarboxylic acid 3-[2-(3-quinolylcarboxyloxy)ethyl]ester-5-methyl ester;
(8) 2,6-dimethyl-4-(2-nitrophenyl)-1,4-dihydropyridine-3,5-dicarboxylic acid 3-(3-nicotinoyloxypropyl)ester-5-methyl ester;
(9) 2,6-dimethyl-4-(2-nitrophenyl)-1,4-dihydropyridine-3,5-dicarboxylic acid 3-[2-(3-thienylcarbonyloxy)ethyl]ester-5-methyl ester;
(10) 2,6-dimethyl-4-(2-nitrophenyl)-1,4-dihydropyridine-3,5-dicarboxylic acid 3-[2-(3-furylcarbonyloxy)ethyl]ester-5-methyl ester;
(11) 2,6-dimethyl-4-(2-nitrophenyl)-1,4-dihydropyridine-3,5-dicarboxylic acid 3-[2-(6-chloronicotinoyloxy)ethyl]ester-5-methyl ester;
(12) 2,6-dimethyl-4-(2-nitrophenyl)-1,4-dihydropyridine-3,5-dicarboxylic acid 3-[2-(3-quinoloylcarbonyloxy)ethyl]ester-5-methyl ester;
(13) 2,6-dimethyl-4-(2-trifluoromethylphenyl)-1,4-dihydropyridine-3,5-dicarboxylic acid 3-(2-nicotinoyloxyethyl)ester-5-methyl ester;
(14) 2,6-dimethyl-4-(2-trifluoromethylphenyl)-1,4-dihydropyridine-3,5-dicarboxylic acid 3-[2-(6-chloronicotinoyloxy)ethyl]ester-5-methyl ester;
(15) 2,6-dimethyl-4-(2-trifluoromethylphenyl)-1,4-dihydropyridine-3,5-dicarboxylic acid 3-[2-(3-quinolycarbonyloxy)ethyl]ester-5-methyl ester;
(16) 2,6-dimethyl-4-(2,3-dichlorophenyl)-1,4-dihydropyridine-3,5-dicarboxylic acid 3-(2-nicotinoyloxyethyl)ester-5-methyl ester;
(17) 2,6-dimethyl-4-(2-nitrophenyl)-1,4-dihydropyridine-3,5-dicarboxylic acid 3-[2-(6-methylnicotinoyloxy)ethyl]ester-5-methyl ester;
(18) 2,6-dimethyl-4-(2-nitrophenyl)-1,4-dihydropyridine-3,5-dicarboxylic acid 3-[2-(6-aminonicotinoyloxy)ethyl]ester-5-methyl ester;
(19) 2,6-dimethyl-4-(2-nitrophenyl)-1,4-dihydropyridine-3,5-dicarboxylic acid 3-[2-(6-acetylaminonicotinoyloxy)ethyl]ester-5-methyl ester;
(20) 2,6-dimethyl-4-(2-nitrophenyl)-1,4-dihydropyridine-3,5-dicarboxylic acid 3-[2-(6-benzoylaminonicotinoyloxy)ethyl]ester-5-methyl ester;
(21) 2,6-dimethyl-4-(2-nitrophenyl)-1,4-dihydropyridine-3,5-dicarboxylic acid 3-[2-(5-chloronicotinoyloxy)ethyl]ester-5-methyl ester;
(22) 2,6-dimethyl-4-(2-trifluoromethylphenyl)-1,4-dihydropyridine-3,5-dicarboxylic acid 3-[2-(6-methylnicotinoyloxy)ethyl]ester-5-methyl ester;
(23) 2,6-dimethyl-4-(2-trifluoromethylphenyl)-1,4-dihydropyridine-3,5-dicarboxylic acid 3-(2-nicotinoyloxyethyl)ester-5-methoxyethyl ester;
(24) 2,6-dimethyl-4-(2-nitrophenyl)-1,4-dihydropyridine-3,5-dicarboxylic acid 3-[2-(6-trichloromethylnicotinoyloxy)ethyl]ester-5-methyl ester;
(25) 2,6-dimethyl-4-(2-nitrophenyl)-1,4-dihydropyridine-3,5-dicarboxylic acid 3-[2-(6-iodonicotinoyloxy)ethyl]ester-5-methyl ester;

(26) 2,6-dimethyl-4-(2-nitrophenyl)-1,4-dihydropyridine-3,5-dicarboxylic acid 3-[2-(6-methoxynicotinoyloxy)ethyl]ester-5-methyl ester;
(27) 2,6-dimethyl-4-(2-nitrophenyl)-1,4-dihydropyridine-3,5-dicarboxylic acid 3-[2-(6-methoxycarbonylnicotinoyloxy)ethyl]ester-5-methyl ester;
(28) 2,6-dimethyl-4-(2-nitrophenyl)-1,4-dihydropyridine-3,5-dicarboxylic acid 3-[2-(6-phenoxynicotinoyloxy)ethyl]ester-5-methyl ester;
(29) 2,6-dimethyl-4-(2-nitrophenyl)-1,4-dihydropyridine-3,5-dicarboxylic acid 3-(2-nicotinoyloxyethyl)ester-5-ethyl ester;
(30) 2,6-dimethyl-4-(2-nitrophenyl)-1,4-dihydropyridine-3,5-dicarboxylic acid 3-(2-nicotinoyloxyethyl)ester-5-isopropyl ester;
(31) 2,6-dimethyl-4-(2-nitrophenyl)-1,4-dihydropyridine-3,5-dicarboxylic acid 3-(2-nicotinoyloxyethyl)ester-5-isobutyl ester;
(32) 2,6-dimethyl-4-(2-nitrophenyl)-1,4-dihydropyridine-3,5-dicarboxylic acid 3-(2-nicotinoyloxyethyl)ester-5-methoxyethyl ester;
(33) 2,6-dimethyl-4-(2-trifluoromethylphenyl)-1,4-dihydropyridine-3,5-dicarboxylic acid 3-[2-(6-methoxynicotinoyloxy)ethyl]ester-5-methyl ester;
(34) 2,6-dimethyl-4-(2-trifluoromethylphenyl)-1,4-dihydropyridine-3,5-dicarboxylic acid 3-(2-nicotinoyloxyethyl)ester-5-isobutyl ester;
(35) 2,6-dimethyl-4-(2-trifluoromethylphenyl)-1,4-dihydropyridine-3,5-dicarboxylic acid 3-[2-(3quinolinecarboxy)ethyl]ester-5-isobutyl ester;
(36) 2,6-dimethyl-4-(2-trifluoromethylphenyl)-1,4-dihydropyridine-3,5-dicarboxylic acid 3-[2-(8-methyl-3-quinolinecarboxy)ethyl]ester-5-isobutyl ester;
(37) 2,6-dimethyl-4-(2-nitrophenyl)-1,4-dihydropyridine-3,5-dicarboxylic acid 3-[2-(3-quinolinecarboxy)ethyl]ester-5-methoxyethyl ester;
(38) 2,6-dimethyl-4-(2-trifluoromethylphenyl)-1,4-dihydropyridine-3,5-dicarboxylic acid 3-[2-(3quinolinecarboxy)ethyl]ester-5-methoxyethyl ester;
(39) 2,6-dimethyl-4-(2-nitrophenyl)-1,4-dihydropyridine-3,5-dicarboxylic acid 3-[2-(6-methoxy-3-quinolinecarboxy)ethyl]ester-5-methyl ester;
(40) 2,6-dimethyl-4-(2-nitrophenyl)-1,4-dihydropyridine-3,5-dicarboxylic acid 3-[2-(8-methyl-3-quinolinecarboxy)ethyl]ester-5-methyl ester;
(41) 2,6-dimethyl-4-(2-nitrophenyl)-1,4-dihydropyridine-3,5-dicarboxylic acid 3-[2-(3-quinolinecarboxy)ethyl]ester-5-isobutyl ester;
(42) 2,6-dimethyl-4-(2-trifluoromethylphenyl)-1,4-dihydropyridine-3,5-dicarboxylic acid 3-[2-(6-methoxy-3-quinolinecarboxy)ethyl]ester-5-isobutyl ester;
(43) 2,6-dimethyl-4-(2-trifluoromethylphenyl)-1,4-dihydropyridine-3,5-dicarboxylic acid 3-[2-(6-methoxy3-quinolinecarboxy)ethyl]ester-5-methyl ester;
(44) 2,6-dimethyl-4-(2-trifluoromethylphenyl)-1,4-dihydropyridine-3,5-dicarboxylic acid 3-[2-(8-methyl-3 quinolinecarboxy)ethyl]ester-5-methyl ester;
(45) 2,6-dimethyl-4-(2-nitrophenyl)-1,4-dihydropyridine- 3,5-dicarboxylic acid 3-[2-(6-methoxy-3-quinolinecarboxy)ethyl]ester-5-isopropyl ester;
(46) 2,6-dimethyl-4-(2-nitrophenyl)-1,4-dihydropyridine-3,5-dicarboxylic acid 3-[2-(4-chloronicotinoyloxy)ethyl]ester-5-methyl ester.

The compounds of the present invention can be prepared by reacting a compound of the formula

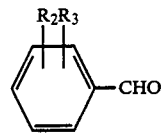

wherein $R_2$ and $R_3$ are as defined above, a compound of the formula

wherein $R_4$ is as defined above, and a compound of the formula

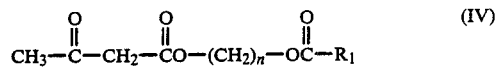

wherein $R_1$ and n are as defined above.

The reaction is preferably conducted using reactants of the formulae II, III and IV in about equal mole amount to each other. However, the proportions of the reactants used may be varied depending on the reaction conditions.

Examples of the compounds represented by the formula II include 2-nitrobenzaldehyde, 3-nitrobenzaldehyde, 2-trifluoromethylbenzaldehyde, 3-trifluoromethylbenzaldehyde, 2,3-dichlorobenzaldehyde, and the like.

Examples of the compounds represented by the formula III include methyl 3-amino crotonate, ethyl 3-aminocrotonate, n-propyl 3-aminocrotonate, i-propyl 3-aminocrotonate, n-butyl 3-aminocrotonate, i-butyl 3-aminocrotonate, tert-butyl 3-aminocrotonate, methoxymethyl 3-aminocrotonate, methoxyethyl 3-aminocrotonate, methoxypropyl 3-aminocrotonate, ethoxymethyl 3-aminocrotonate, ethoxyethyl 3-aminocrotonate, ethoxypropyl 3-aminocrotonate, propoxymethyl 3-aminocrotonate, propoxyethyl 3-aminocrotonate, propoxypropyl 3-aminocrotonate, and the like.

Examples of the compounds represented by the formula IV include those wherein n is 2 or 3, $R_1$ is 2-furyl, 3-furyl, 2-thienyl, 3-thienyl, 2-pyrroyl, 3-pyrroyl, 2-pyranyl, 3-pyranyl, 4-pyranyl, 2-pyridyl, 3-pyridyl, 4-pyridyl, 3-isooxazolyl, 4-isooxazolyl, 5-isooxazolyl, 3-isothiazolyl, 4-isothiazolyl, 5-isothiazolyl, 2-imidazolyl, 4-imidazolyl, 2-morpholinyl, 3-morpholinyl, 2-pyrimidinyl, 4-pyrimidinyl, 5-pyrimidinyl, 2-pyrazinyl, 3-pyridazinyl and 4-pyridazinyl, or these heterocyclic groups may be substituted with one or more substituents selected from fluorine, chlorine, bromine, iodine, trichloromethyl, trifluoromethyl, amino, acetylamino, benzoylamino, methoxy, ethoxy, propoxy, phenoxy, methoxycarbonyl, ethoxycarbonyl, methyl, ethyl, n-propyl, i-propyl, n-butyl, i-butyl and tert-butyl; and also $R_1$ is 2-quinolyl, 3-quinolyl, 4-quinolyl, 1-isoquinolyl, 3-isoquinolyl, 4-isoquinolyl, 2-quinazolinyl, 4-quinazolinyl and quinoxalinyl, and further benzene ring forming these groups may be substituted with one or more substituents selected from methyl, ethyl, n-propyl, i-propyl, n-butyl, i-butyl, tert-butyl, methoxy, ethoxy and propoxy.

The reaction can be effected using an organic solvent as a reaction medium. Preferred solvents include an alcohol such as methanol, ethanol, i-propanol or n- butanol; a lower dialkyl ether, e.g., diethylether; a cyclic ether such as tetrahydrofuran or dioxane; a lower dialkylformamide, e.g., dimethylformamide; dimethylsulfoxide; and a liquid heterocyclic base, e.g., pyridine.

The reaction may also be carried out in the absence of a reaction medium.

The reaction temperature can be from about 20° C. to 150° C., preferably from 50° C. to 100° C.

The reaction can be effected at a temperature at which the reaction medium is boiling. The reaction can be carried out at atmospheric pressure, optionally under elevated pressure. The reaction is usually completed under the above reaction conditions during the time from 45 minutes to 10 hours.

Further, the compounds of the present invention can be prepared by reacting a compound of the formula

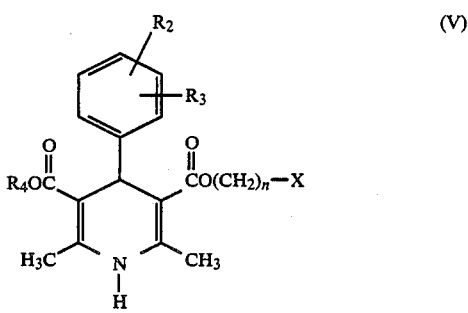

wherein $R_2$, $R_3$, $R_4$ and n are as defined above, and X represents a halogen atom, a mesyloxy group, a benzene-sulfonyloxy group or a tosyloxy group, and a compound of the formula

wherein $R_1$ is as defined above and M represents an alkali metal or an alkaline earth metal.

Examples of the compounds represented by the formula V include those wherein n is 2 or 3; $R_2$ is hydrogen when $R_3$ is nitro or trifluoromethyl; or $R_2$ is nitro or trifluoromethyl when $R_3$ is hydrogen; or both $R_2$ and $R_3$ are chlorine; and further $R_4$ is methyl, ethyl, n-propyl, i-propyl, n-butyl, i-butyl, tert-butyl, methoxymethyl, methoxyethyl, methoxypropyl, ethoxymethyl, ethoxyethyl, ethoxypropyl, propoxymethyl, propoxyethyl or propoxypropyl; and further X is chlorine, bromine, iodine, mesyloxy, benzenesulfonyloxy or tosyloxy.

Examples of the compounds represented by the formula VI include those wherein $R_1$ is 2-furyl, 3-furyl, 2-thienyl, 3-thienyl, 2-pyrrolyl, 3-pyrrolyl, 2-pyranyl, 3-pyranyl, 4-pyranyl, 2-pyridyl, 3-pyridyl, 4-pyridyl, 3-isooxazolyl, 4-isooxazolyl, 5-isooxazolyl, 3-isothiazolyl, 4-isothiazolyl, 5-isothiazolyl, 2-imidazolyl, 4-imidazolyl, 2-morpholinyl, 3-morpholinyl, 2-pyrimidinyl, 4-pyrimidinyl, 5-pyrimidinyl, 2-pyridozinyl, 3-pyridazinyl and 4-pyridazinyl; or these heterocyclic groups may be substituted with one or more substituents selected from fluorine, chlorine, bromine, iodine, trichloromethyl, trifluoromethyl, amino, acetylamino, benzoylamino, methoxy, ethoxy, propoxy, phenoxy, methoxycarbonyl, ethoxycarbonyl, methyl, ethyl, n-propyl, i-propyl, n-butyl, i-butyl and tert-butyl; and also $R_1$ is 2-quinolyl, 3-quinolyl, 4-quinolyl, 1-isoquinolyl, 3-isoquinolyl, 4-isoquinolyl, 2-quinazolinyl, 4-quinazolinyl and quinoxalinyl, and further benzene ring forming these groups may be substituted with one or more substituents selected from methyl, ethyl, n-propyl, i-propyl, n-butyl, i-butyl, tert-butyl, methoxy, ethoxy and propoxy, and M is sodium, potassium, magnesium or calcium.

The reaction can be carried out preferably in the presence of an inert organic solvent. Suitable solvents include N,N-dimethylformamide, N,N-dimethylacetamide, dimethyl sulfoxide, hexamethyl phosphoamide, dioxane, acetonitrile, N-methylmorpholine, 1,2-dimethoxyethane, and the like. The reaction temperature is suitably from 80° C. to 160° C. Under the above conditions, the reaction is usually completed in a few hours.

Pharmaceutically acceptable acid addition salts of the compounds of the formula I according to the present invention may be prepared by the application or adaptation of known methods for the preparation of salts of organic bases, for example, by reacting the compounds of the formula I with the appropriate acid in a suitable solvent. Examples of addition salts include salts derived from inorganic and organic acids such as, without limitation, hydrochloric acid, phosphoric acid, sulfuric acid, acetic acid, tartaric acid, lactic acid, succinic acid, citric acid, maleic acid, sorbic acid, salicyclic acid, phthalic acid, and the like.

The new compounds may, depending on the choice of starting materials and process, be present as optical isomers or racemate.

The racemates obtained can be separated according to known methods, e.g., by means of microorganisms, or by a reaction with optically active acids forming salts of the compound, and separating the salts thus obtained, e.g., by means of the different solubility of the diastereomeric salts, from which the isomers may be set free by the action of a suitable agent. Suitably useable optically active acids are e.g., the L- and D-forms of tartaric acid, di-o-tolyltartaric acid, malic acid, mandelic acid, camphorsulfonic acid or quinic acid. Preferably the more active part of the two isomers is isolated.

The compounds of the present invention have marked inhibiting activity of calcium influx into cells as will be evident from the below-mentioned pharmacological test results, with the result of the use as vasodilator and antihypertensive agents. Thus, the compounds of the present invention can be used for treatment of a variety of diseases including cardiac diseases such as angina pectoris, arrhythmia and acute heart failure, cerebrovascular diseases such as cerebral infarction and hypertension.

In clinical use the compounds of the invention are usually administered orally, or parenterally in the form of a pharmaceutical preparation, which contains the active ingredient as free base in combination with pharmaceutically acceptable additives.

Thus the mentioning of the new compounds of the invention is here related to the free amine base even if the compounds are generally or specifically described, provided that the context in which such expressions are used, e.g., in Example 1, with this broad meaning should not correspond. The additives may be a solid, semisolid or liquid diluent or a capsule. These pharmaceutical preparations are a further object of the invention. Usually the amount of active ingredient is between 0.1 and 99% by weight of the preparation, suitably between 0.5 and 20% by weight in preparations for injection and between 2 and 50% by weight in preparations for oral administration.

In the preparation of pharmaceutical preparations containing a compound of the present invention in the form of dosage units for oral administration the compound may be mixed with a solid, pulverulent additives, e.g., with lactose, saccharose, sorbitol, mannitol, starch, such as potato starch, corn starch, amylopectin, cellulose derivatives or gelatine, as well as with an lubricant such as magnesium stearate, calcium stearate, polyethyleneglycol waxes or the like, and be pressed into tablets. If coated tablets are wanted, the above prepared core may be coated with concentrated solution of sugar, which solution may contain, e.g., gum arabicum, gelatine, talc, titandioxide or the like.

In the preparation of soft gelatine capsules which consist of gelatine and, e.g., glycerine, or in the preparation of similar closed capsules, the active compound is mixed with a vegetable oil. Hard gelatine capsules may contain granules of the active compound in combination with a solid, pulverulent additives as lactose, saccharose, sorbitol, mannitol, starch (as, e.g., potato starch, corn starch or amylopectin), cellulose derivatives or gelatine.

Dosage units for rectal administration may be prepared in the form of suppositories, which contain the active ingredient in a mixture with a neutral fat base, or they may be prepared in the form of gelatine-rectal capsules which contain the active substance in a mixture with a vegetable oil or paraffin oil.

Liquid preparations for oral administration may be present in the form of sirups or suspensions, e.g., solutions containing from about 0.01% by weight to about 0.1% by weight of the active ingredient described, glycerol and propylene glycol.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed with continuous and constant mixing with the binding agent solution and are moistened so that the solution is uniformly divided in the mass without over-moistening any parts. The amount of solvent is usually so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the damp degree of the granulate is of outmost importance for the following process and for the feature of the tablets. Drying in a fluid bed may possibly be used. In this case the mass is not put on a tray but is poured into a container having a net bottom.

After the drying step the granules are sieved so that the particle size wanted is obtained. Under certain circumstances powder has to be removed.

To the so called final mixture, disintegrating, lubricant and excipient are added. After this mixture the mass shall have its right composition for the tabletting step.

Many tablets, especially those which are rough or bitter, are coated with a coating. This means that they are coated with a layer of sugar or some other suitable coating.

The daily dose of the active ingredient varies and is dependent on the type of administration, but as a general rule it is 1 to 100 mg/day of active ingredient at peroral administration.

BEST MODE FOR CARRYING OUT THE INVENTION

The following examples will serve to further typify the nature of the present invention without being a limitation on the scope thereof, the scope being defined solely by the appended claims.

EXAMPLE 1

2,6-Dimethyl-4-(2-nitrophenyl)-1,4-dihydropyridine-3,5-dicarboxylic acid 3-(2-nicotinoyloxyethyl)ester-5-methyl ester

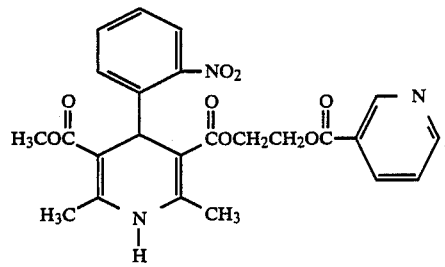

A solution of 1.3 g of 2-nitrobenzaldehyde, 1.0 g of methyl 3-aminocrotonate and 2.2 g of 2-nicotinoyloxyethyl acetoacetate in 3 ml of isopropyl alcohol was heated under reflux for 6 hours. The reaction mixture was concentrated under reduced pressure, an oily residue was subjected to silica gel column chromatography with ethyl acetate as an eluent. Recrystallization from acetone gave the title compound. Yield 1.1 g (27%), m.p. 160°–161° C.

EXAMPLE 2

2,6-Dimethyl-4-(3-nitrophenyl)-1,4-dihydropyridine-3,5-dicarboxylic acid 3-(2-nicotinoyloxyethyl)ester-5-methyl ester

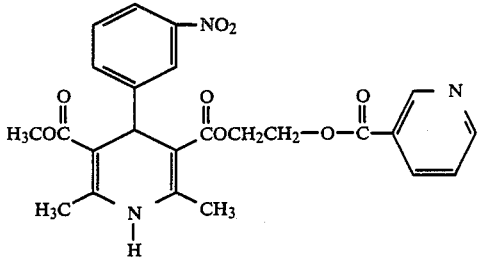

A mixture of 1.0 g of 2,6-dimethyl-4-(3-nitrophenyl)-1,4-dihydropyridine-3,5-dicarboxylic acid 3-(2-chloroethyl)ester-5-methyl ester and 0.55 g of sodium nicotinate in 7 ml of N,N-dimethylformamide was stirred at 120°–130° C. in an argon stream for 4 hours. The reaction product was suction filtered, and the filtrate was concentrated under reduced pressure. The residue was subjected to silica gel colum chromatography with ethyl acetate-n-hexane (a volume ratio 5:1) as an eluent, whereby the title compound was prepared as crystal. Yield 1.1 g (90%), m.p. 135°–136° C.

EXAMPLES 3–8

Following the same procedure as described in Example 2, compounds of the undermentioned general formula were prepared as shown in Table 1 below.

TABLE 1

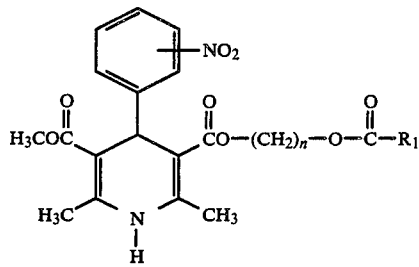

| Example | Position of NO₂ | n | R₁ | Yield | Melting point |
|---|---|---|---|---|---|
| 3 | 3 | 2 |  | 73% | 175–176° C. |
| 4 | 3 | 2 |  | 70% | 153–154° C. |
| 5 | 3 | 2 |  | 58% | 136–138° C. |
| 6 | 3 | 2 |  | 67% | 152–153° C. |
| 7 | 3 | 2 | 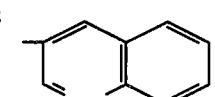 | 57% | 197.5–198.5° C. |
| 8 | 2 | 3 |  | 43% | 171–173° C. |

EXAMPLE 9

2,6-Dimethyl-4-(2-nitrophenyl)-1,4-dihydropyridine-3,5-dicarboxylic acid 3-2-(3-thienylcarbonyloxy)ethyl ester-5-methyl ester

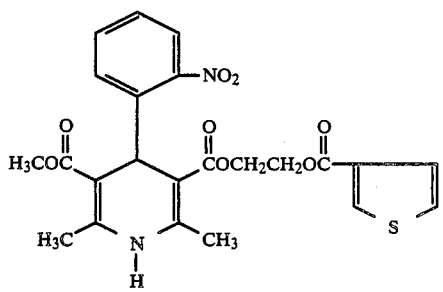

A mixture of 1.2 g of 2,6-dimethyl-4-(2-nitrophenyl)-1,4-dihydropyridine-3,5-dicarboxylic acid 3-(2-chloroethyl)ester-5-methyl ester and 0.5 g of sodium 3-thienylcarboxylate in 10 ml of N,N-dimethylformamide was stirred at 120°–130° C. in an argon stream for 2 hours. To the reaction product was added ethyl acetate. insolubles were removed by suction filtration and the filtrate was concentrated under reduced pressure. The residue was subjected to silica gel column chromatography with ethyl acetate-n-hexane (a volume ratio 1:1) as an eluent, whereby the title compound was prepared as non-crystalline powder. Yield 0.8 g (54%).

This compound as prepared was measured for NMR. The results are shown below.

$^1$H NMR (CDCl₃) δ: 2.29 (s, 3H), 2.36 (s, 3H), 3.55 (s, 3H), 4.34–4.40 (m, 4H), 5.78 (s, 1H), 6.03 (s, 1H), 7.11–7.70 (m, 6H), 8.00 (d-d, 1H).

EXAMPLES 10–12

Following the same procedure as described in Example 9, there were prepared the compounds as shown in Table 2 below.

TABLE 2

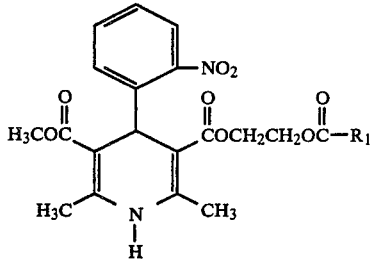

| Example | R₁ | Yield | Physical properties |
|---|---|---|---|
| 10 |  | 53% | Non-crystalline powder $^1$H NMR (CDCl₃)δ: 2.29(s, 3H), 2.36(s, 3H), 3.56(s, 3H), 4.22–4.43(m, 4H), 5.77(s, 1H), 6.11(s, 1H), 6.68(d-d, 1H), 7.12–7.66(m, 5H), 7.91(d-d, 1H). |
| 11 |  | 69% | Non-crystalline powder $^1$H NMR (CDCl₃)δ: 2.30(s, 3H), 2.37(s, 3H), 3.55(s, 3H), 4.34–4.49(m, 4H), 5.76(s, 1H), 5.97(s, 1H), 7.12–7.66(m, 5H), 8.18(d-d, 1H), 8.85(d, 1H). |

TABLE 2-continued

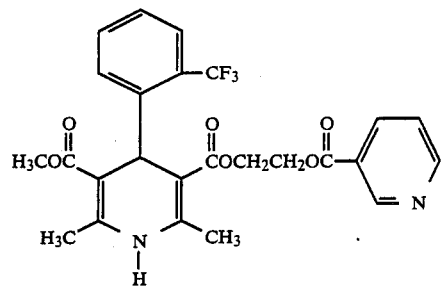

| Example | R₁ | Yield | Physical properties |
|---|---|---|---|
| 12 | (quinoline) | 49% | M.P. 159–160° C. |

EXAMPLE 13

2,6-Dimethyl-4-(2-trifluoromethylphenyl)-1,4-dihydropyridine-3,5-dicarboxylic acid 3-(2-nicotinoyloxyethyl)ester-5-methyl ester A mixture of 1.4 g of 2,6-dimethyl-4-(2-trifluoromethylphenyl)-1,4-dihydropyridine-3,5-dicarboxylic acid 3-(2-chloroethyl)ester-5-methyl ester and 0.8 g of sodium nicotinate in 8 ml of N,N-dimethylformamide was stirred at 120°–130° C. in an argon stream for 5 hours. To the reaction product was added ethyl acetate, insolubles were removed by suction filtration and the filtrate was concentrated under reduced pressure. The residue was subjected to silica gel column chromatography with ethyl acetate as an eluent, whereby the title compound was prepared as crystals. Yield 0.8 g (47%), m.p. about 139° C. (end point).

This compound as prepared was measured for NMR. The results are shown below.

$^1$H NMR (CDCl₃) δ: 2.29 (s, 3H), 2.33 (s, 3H), 3.56 (s, 3H), 4.29–4.47 (m, 4H), 5.56 (s, 1H), 5.98 (s, 1H), 7.11–7.54 (m, 5H), 8.22 (d-t, 1H), 8.78 (d-d, 1H), 9.10 (d, 1H).

EXAMPLES 14–16

Following the same procedure as described in Example 13, there were prepared the compounds as shown in Table 3 below.

TABLE 3

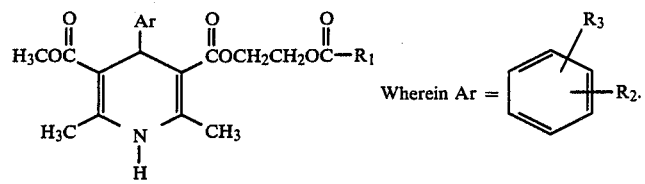

| Example | Ar | R₁ | Yield | Physical properties |
|---|---|---|---|---|
| 14 | (phenyl-CF₃) | (pyridyl-Cl) | 66% | Non-crystalline powder, $^1$H NMR (CDCl₃) δ: 2.29(s, 3H), 2.33(s, 3H), 3.57(s, 3H), 4.26–4.49 (m, 4H), 5.55(s, 1H), 5.90(s, 1H), 7.16–7.54 (m, 5H), 8.15(d-d, 1H), 8.86(d-d, 1H). |
| 15 | (phenyl-CF₃) | (quinoline) | 65% | M.P. 160–161° C. (end point) $^1$H NMR (CDCl₃) δ: 2.28(s, 3H), 2.34(s, 3H), 3.52(s, 3H), 4.37–4.56(m, 4H), 5.57(s, 1H), 5.96(s, 1H), 7.08(t, 1H), 7.27–7.36(m, 2H), 7.52(d, 1H), 7.64(d-d, 1H), 7.85(t, 1H), 7.94(d, 1H), 8.18(d, 1H), 8.77(d, 1H), 9.35(d, 1H). |
| 16 | (phenyl-Cl,Cl) | (pyridyl) | 64% | M.P. 144–145° C. |

EXAMPLES 17–38

Following the same procedure as described in Example 13, there were prepared the compounds as shown in Table 4 below.

TABLE 4

Structure:

R₄OC(=O)–C(=C(CH₃)–NH–C(CH₃)=)–CH(Ar)–C(=)–CO(CH₂)₂OC(=O)–R₁ where Ar = phenyl with R₂ (ortho) and R₃ (meta) substituents; central ring is 1,4-dihydropyridine with H₃C and CH₃ at 2,6-positions and NH.

| Ex. | R₂ | R₄ | R₁ | Yield | Physical properties |
|---|---|---|---|---|---|
| 17 | NO₂ | CH₃ | 2-methylpyridin-4-yl | 25% | Non-crystalline yellow powder. ¹H NMR(CDCl₃)δ: 2.28(s,3H), 2.36(s,3H), 2.64(s,3H), 3.53(s,3H), 4.30–4.60(m,4H), 5.78(s,1H), 7.13(t,1H), 7.25(d,1H), 7.40(t,1H), 7.55(d-d,2H), 8.10(d-d,1H), 8.98(d,1H) |
| 18 | NO₂ | CH₃ | 2-aminopyridin-4-yl | 19% | Non-crystalline yellow powder. ¹H NMR(CDCl₃)δ: 2.28(s,3H), 2.35(s,3H), 3.55(s,3H), 4.38(br.s,4H), 5.30(br.s,2H), 5.78(s,1H), 6.48(s,1H), 7.15(t-d,1H), 7.33–7.65(m,4H), 7.90(d-d,1H), 8.58(d,1H) |
| 19 | NO₂ | CH₃ | 2-(acetylamino)pyridin-4-yl (NHCOCH₃) | 41% | Non-crystalline yellow powder. ¹H NMR(CDCl₃)δ: 2.28(s,3H), 2.30(s,3H), 2.35(s,3H), 3.54(s,3H), 4.30–4.60(m,4H), 5.78(s,1H), 6.70(s,1H), 7.15(t,1H), 7.30–7.60(m,3H), 8.10–8.30(m,2H), 8.80(d-d,1H), 9.15(br.s,1H) |
| 20 | NO₂ | CH₃ | 2-(benzoylamino)pyridin-4-yl (NHCO–C₆H₅) | 12% | Non-crystalline yellow powder. ¹H NMR(CDCl₃)δ: 2.28(s,3H), 2.35(s,3H), 3.54(s,3H), 4.30–4.50(m,4H), 5.78(s,1H), 6.40(br.s,1H), 7.15(t-d,1H), 7.40(t,1H), 7.45–7.65(m,5H), 7.95(d-d,2H), 8.20(d-d,1H), 7.43(d,1H), 8.75(d,1H), 9.14(br.s,1H) |

TABLE 4-continued

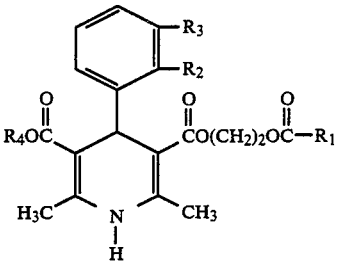

| Ex. | R₂ | R₄ | R₁ | Yield | Physical properties |
|---|---|---|---|---|---|
| 21 | NO₂ | CH₃ | 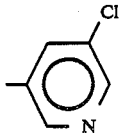 | 20% | Non-crystalline yellow powder |
| | | | | | ¹H NMR(CDCl₃)δ: 2.30(s,3H), 2.37(s,3H), 3.54(s,3H), 4.35–4.56 (m,4H), 5.77(s,1H), 6.10(br.s,1H), 7.15 (t-d,1H), 7.35–7.60(m, 3H), 8.18(t,1H), 8.74 (d,1H), 8.95(d,1H). |
| 22 | CF₃ | CH₃ | 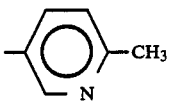 | 62% | Non-crystalline pale yellow white powder |
| | | | | | ¹H NMR(CDCl₃)δ: 2.26(s,3H), 2.30(s,3H), 2.65(s,3H), 3.56(s,3H), 4.25–4.50(m,4H), 5.55 (s,1H), 6.66(br.s,1H), 7.10–7.45(m,4H), 7.55 (d,1H), 8.10(d-d,1H), 9.00(d,1H) |
| 23 | CF₃ | CH₂CH₂OCH₃ | 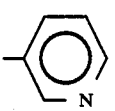 | 75% | Crystalline white powder m.p. 123–124° C. |
| | | | | | ¹H NMR(CDCl₃)δ: 2.25(s,3H), 2.31(s,3H), 3.30(s,3H), 3.45–3.65 (m,2H), 3.94–4.10(m,1H), 4.22–4.50(m,5H), 5.58 (s,1H), 6.20(br.s,1H), 7.24(t,1H), 7.30–7.60 (m,4H), 8.20(d,1H), 8.78(d,1H), 9.10(s,1H) |
| 24 | NO₂ | CH₃ | 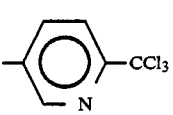 | 28% | Non-crystalline yellow powder |
| | | | | | ¹H NMR(CDCl₃)δ: 2.29(s,3H), 2.37(s,3H), 3.54(s,3H), 4.30–4.65 (m,4H), 5.77(s,1H), 6.69(br,1H), 7.07–7.20 (m,1H), 7.32–7.58(m, 3H), 8.09(d-d,1H), 8.38 (d-d,1H), 9.09(d-d,1H) |
| 25 | NO₂ | CH₃ | 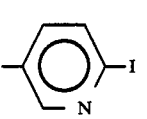 | 29% | Non-crystalline yellow powder |
| | | | | | ¹H NMR(CDCl₃)δ: 2.30(s,3H), 2.36(s,3H), |

TABLE 4-continued

Structure: 4-aryl-1,4-dihydropyridine with $R_4OC(=O)-$ at one 3-position and $-C(=O)O(CH_2)_2OC(=O)-R_1$ at the other; aryl bears $R_3$ and $R_2$; 2,6-dimethyl; N-H.

| Ex. | $R_2$ | $R_4$ | $R_1$ | Yield | Physical properties |
|---|---|---|---|---|---|
| | | | | | 3.55(s,3H), 4.25–4.58 (m,4H), 5.75(s,1H), 5.96(br,1H), 7.10–7.22 (m,1H), 7.32–7.60(m, 3H), 7.82(d,2H), 8.77 (d-d,1H) |
| 26 | $NO_2$ | $CH_3$ | 2-methoxypyridin-4-yl (pyridine with $-OCH_3$) | 39% | Non-crystalline yellow powder<br><br>$^1$H NMR(CDCl$_3$)δ: 2.30(s,3H), 2.37(s,3H), 3.55(s,3H), 4.00(s,3H), 4.25–4.53(m,4H), 5.78 (s,1H), 5.97(br,1H), 6.74(d,1H), 7.10–7.22 (m,1H), 7.35–7.61(m, 3H), 8.05(d-d,1H), 8.70 (d,1H) |
| 27 | $NO_2$ | $CH_3$ | 2-(methoxycarbonyl)pyridin-4-yl (pyridine with $-COOCH_3$) | 34% | Non-crystalline yellow powder<br><br>$^1$H NMR(CDCl$_3$)δ: 2.30(s,3H), 2.36(s,3H), 3,53(s,3H), 4.05(s,3H), 4.30–4.60(m,4H), 5.77 (s,1H), 6.29(br,1H), 7.08–7.20(m,1H), 7.32–7.60(m,3H), 8.19(d,1H), 8.38(d-d,1H), 9.18(d,1H) |
| 28 | $NO_2$ | $CH_3$ | 2-phenoxypyridin-4-yl | 57% | Non-crystalline yellow powder<br><br>$^1$H NMR(CDCl$_3$)δ: 2.28(s,3H), 2.34(s,3H), 3.53(s,3H), 4.25–4.58 (m,4H), 5.76(s,1H), 6.13(br,1H), 6.91(d,1H), 7.07–7.70(m,9H), 8.19 (d-d,1H), 8.67(d,1H) |
| 29 | $NO_2$ | $C_2H_5$ | pyridin-4-yl | 46% | Non-crystalline yellow powder<br><br>$^1$H NMR(CDCl$_3$)δ: 1.12(t,3H), 2.31(s,3H), 2.34(s,3H), 3.98(q,1H), 4.08(q,1H), 4.30–4.53(m,4H), 5.83 (s,1H), 5.93(br,1H), 7.09–7.20(m,1H), 7.35–7.62(m,4H), 8.25(d-d-d, 1H), 8.77(d-d,1H), 9.09(d-d,1H) |

TABLE 4-continued

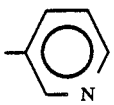

| Ex. | $R_2$ | $R_4$ | $R_1$ | Yield | Physical properties |
|---|---|---|---|---|---|
| 30 | $NO_2$ | $i$-$C_3H_7$ | 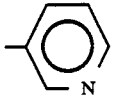 | 69% | Yellow oily product<br>$^1$H NMR(CDCl$_3$)δ:<br>0.95(d,3H), 1.16(d,3H),<br>2.29(s,3H), 2.32(s,3H),<br>4.30–4.55(m,4H), 4.92<br>(sep,1H), 5.87(s,1H),<br>6.08(b,1H), 7.10–7.22<br>(m,1H), 7.34–7.70(m,<br>4H), 8.31(d-d-d,1H),<br>8.77(d-d,1H), 9.12(d,1H) |
| 31 | $NO_2$ | $i$-$C_4H_9$ | 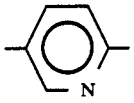 | 55% | Yellow oily product<br>$^1$H NMR(CDCl$_3$)δ:<br>0.73(d,3H), 0.76(d,3H),<br>1.82(n,1H), 2.33(s,6H),<br>3.65–3.90(m,2H), 4.27–<br>4.53(m,4H), 5.80(br,1H),<br>5.82(s,1H), 7.10–7.22<br>(m,1H), 7.35–7.65(m,4H),<br>8.28(d-d-d,1H), 8.77<br>(d-d,1H), 9.10(d-d,1H) |
| 32 | $NO_2$ | $CH_3OCH_2CH_2$ | | 47% | Crystalline yellow<br>powder m.p. 137–139° C.<br>$^1$H NMR(CDCl$_3$)δ:<br>2.28(s,3H), 2.35(s,3H),<br>3.27(s,3H), 3.37–3.65<br>(m,2H), 3.93–4.60(m,<br>4H), 5.84(s,1H), 6.07<br>(br,1H), 7.07–7.20(m,<br>1H), 7.30–7.66(m,4H),<br>8.23(d-d-d,1H), 8.77<br>(d-d,1H), 9.08(d,1H) |
| 33 | $CF_3$ | $CH_3$ | 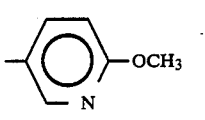 | 73% | Non-crystalline colorless<br>powder<br>$^1$H NMR(CDCl$_3$)δ:<br>2.30(s,3H), 2.33(s,<br>3H), 3.57(s,3H), 4.00<br>(s,3H), 4.20–4.50(m,<br>4H), 5.57(br,1H), 5.79<br>(s,1H), 6.74(d,1H),<br>7.10–7.22(m,1H), 7.29–<br>7.57(m,3H), 8.06(d-d,<br>1H), 8.74(d,1H) |
| 34 | $CF_3$ | $i$-$C_4H_9$ | 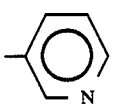 | 44% | Colorless oily product<br>$^1$H NMR(CDCl$_3$)δ: |

TABLE 4-continued

Structure:

$R_4OC(=O)$ and $CO(CH_2)_2OC(=O)-R_1$ groups on a 1,4-dihydropyridine ring with $H_3C$ and $CH_3$ at 2,6-positions, NH, and a phenyl substituent bearing $R_2$ and $R_3$.

| Ex. | R₂ | R₄ | R₁ | Yield | Physical properties |
|---|---|---|---|---|---|
| | | | | | 0.77(d,6H), 1.86(n,1H), 2.29(s,3H), 2.31(s,3H), 3.69(d-d,1H), 3.88(d-d, 1H), 4.27–4.60(m,4H), 5.57(s,1H), 5.83(br,1H), 7.08–7.21(m,1H), 7.28–7.60(m,4H), 8.24(d-d-d, 1H), 8.78(d-d,1H), 9.11(d-d,1H) |
| 35 | CF₃ | i-C₄H₉ | 3-quinolinyl | 36% | Colorless oily product<br><br>¹H NMR(CDCl₃)δ: 0.72(d,6H), 1.79(n,1H), 2.28(s,3H), 2.32(s,3H), 3.67(d-d,1H), 3.84(d-d, 1H), 4.30–4.60(m,4H), 5.59(s,1H), 5.81(br,1H), 7.03–7.15(m,1H), 7.30–8.20(m,7H), 8.79(d,1H), 9.35(d,1H) |
| 36 | CF₃ | i-C₄H₉ | 8-methyl-3-quinolinyl | 33% | Non-crystalline colorless powder<br><br>¹H NMR(CDCl₃)δ: 0.72(d,6H), 1.83(n,1H), 2.29(s,3H), 2.33(s,3H), 2.85(s,3H), 3.67(d-d, 1H), 3.84(d-d,1H), 4.27–4.60(m,4H), 5.58(s, 1H), 5.64(br,1H), 7.03–7.15(m,1H), 7.25–7.82 (m,6H), 8.75(d,1H), 9.38(d,1H) |
| 37 | NO₂ | CH₃OCH₂CH₂ | 3-quinolinyl | 53% | Crystalline yellow powder m.p. 100–102° C.<br><br>¹H NMR(CDCl₃)δ: 2.27(s,3H), 2.36(s,3H), 3.22(s,3H), 3.37–3.66 (m,2H), 3.88–4.67(m, 6H), 5.85(s,1H), 6.13 (br,1H), 6.97–7.10(m, 1H), 7.27–8.20(m,7H), 8.82(d,1H), 9.33(d,1H) |
| 38 | CF₃ | CH₃OCH₂CH₂ | 3-quinolinyl | 80% | Crystalline pale yellow powder m.p. 74–76° C.<br><br>¹H NMR(CDCl₃)δ: 2.24(s,3H), 2.33(s,3H), 3.24(s,3H), 3.41–3.57 (m,2H), 3.94–4.05(m, |

TABLE 4-continued

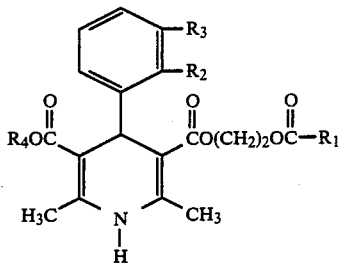

| Ex. | R₂ | R₄ | R₁ | Yield | Physical properties |
|---|---|---|---|---|---|
| | | | | | 1H), 4.22–4.52(m,5H), 5.60(s,1H), 6.17(s, 1H), 7.03–7.10(m,1H), 7.27–8.20(m,7H), 8.77 (d,1H), 9.35(d,1H) |
| 39 | NO₂ | CH₃ | 6-methoxyquinolin-3-yl | 49% | Non-crystalline yellow powder |
| | | | | | $^1$H NMR(CDCl₃)δ: 2.29(s,3H), 2.39(s,3H), 3.51(s,3H), 3.98(s,3H), 4.37–4.56(m,4H), 5.79 (s,1H), 5.92(br,1H), 6.98–7.10(m,1H), 7.18–7.55(m,5H), 8.06(d,1H), 8.72(d,1H), 9.15(s,1H) |
| 40 | NO₂ | CH₃ | 8-methylquinolin-3-yl | 57% | Non-crystalline yellow powder |
| | | | | | $^1$H NMR(CDCl₃)δ: 2.30(s,3H), 2.39(s,3H), 2.85(s,3H), 3.51(s,3H), 4.34–4.67(m,4H), 5.79 (s,1H), 5.83(br,1H), 6.96–7.08(m,1H), 7.27–7.83(m,6H), 8.75(d, 1H), 9.33(d,1H) |
| 41 | NO₂ | i-C₄H₉ | quinolin-3-yl | 56% | Non-crystalline yellow powder |
| | | | | | $^1$H NMR(CDCl₃)δ: 0.68(d,3H), 0.71(d,3H), 1.81(n,1H), 2.31(s,3H), 2.33(s,3H), 3.70(d-d,1H), 3.78(d-d,1H), 4.30–4.64(m,4H), 5.84(s,1H), 6.25(br,1H), 7.00–8.20 (m,8H), 8.85(d,1H), 9.35(d,1H) |
| 42 | CF₃ | i-C₄H₉ | 6-methoxyquinolin-3-yl | 32% | Non-crystalline colorless powder |
| | | | | | $^1$H NMR(CDCl₃)δ: 0.72(d,6H), 1.83(n, 1H), 2.27(s,3H), 2.31 (s,3H), 3.68(d-d,1H), 3.83(d-d,1H),3.96(s, 3H), 4.28–4.62(m,4H), 5.59(s,1H), 6.10(br,1H), 7.03–7.60(m,6H), 8.06 (d,1H), 8.70(d,1H), 9.20(d,1H) |

TABLE 4-continued

[Structure: 1,4-dihydropyridine with aryl group bearing R3, R2; R4OC(O)- on one side; -C(O)O(CH2)2OC(O)-R1 on other side; H3C and CH3 at 2,6 positions; NH]

| Ex. | R2 | R4 | R1 | Yield | Physical properties |
|-----|-----|-----|-----|-------|---------------------|
| 43 | CF3 | CH3 | 6-methoxyquinolin-3-yl | 71% | Non-crystalline colorless powder<br>$^1H$ NMR(CDCl$_3$)δ: 2.29(s,3H), 2.34(s,3H), 3.52(s,3H), 3.97(s,3H), 4.28–4.56(m,4H), 5.56(s,1H), 5.82(br,1H), 7.02–7.54(m,6H), 8.06(d,1H), 8.68(d,1H), 9.19(d,1H) |
| 44 | CF3 | CH3 | 8-methylquinolin-3-yl | 54% | Non-crystalline colorless powder<br>$^1H$ NMR(CDCl$_3$)δ: 2.30(s,3H), 2.35(s,3H), 2.84(s,3H), 3.52(s,3H), 4.25–4.55(m,4H), 5.57(s,1H), 5.68(br,1H), 7.02–7.80(m,7H), 8.72(d,1H), 9.37(d,1H) |
| 45 | NO2 | i-C3H7 | 6-methoxyquinolin-3-yl | 62% | Non-crystalline yellow powder<br>$^1H$ NMR(CDCl$_3$)δ: 0.93(d,3H), 1.13(d,3H), 2.31(s,6H), 3.97(s,3H), 4.32–4.59(m,4H), 4.84–4.96(m,1H), 5.89(s,1H), 5.99(br,1H), 7.05–7.65(m,6H), 8.05(d,1H), 8.75(d,1H), 9.20(d,1H) |
| 46 | NO2 | CH3 | 4-chloropyridin-3-yl | 47% | Non-crystalline yellow powder<br>$^1H$ NMR(CDCl$_3$)δ: 2.30(s,3H), 2.38(s,3H), 3.55(s,3H), 4.36–4.53(m,4H), 5.78(s 1H), 6.09(s,1H), 7.10–7.18(m,1H), 7.35–7.59(m,4H), 8.59(d,1H), 8.91(s,1H) |

The novel compounds as prepared in the abovementioned examples were individually measured for Ca-blocking potency thereof in accordance with the method of M. Fiol de Cureo et al. (Arch. int. Pharmacodyn., 263, 28–39, 1983). This method is to evaluate each compound to be tested with respect to Ca-blocking potency on the basis of 50% inhibiting concentration of a spontaneous contraction of an isolated rat portal vein. The results are shown in terms of a relative activity to Nifedipine (Nifedipine=1) in Table 5.

TABLE 5
| Example | R$_2$ | R$_4$ | R$_1$ | Specific potency |
|---|---|---|---|---|
| 1 | NO$_2$ | CH$_3$ | 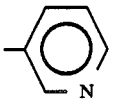 | 3.1 |
| 9 | NO$_2$ | CH$_3$ | 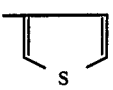 | 5.9 |
| 10 | NO$_2$ | CH$_3$ | 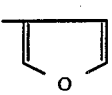 | 3.4 |
| 11 | NO$_2$ | CH$_3$ | 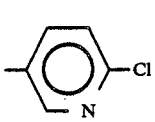 | 40.6 |
| 12 | NO$_2$ | CH$_3$ | 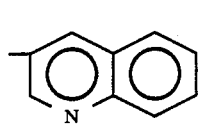 | 40.6 |
| 13 | CF$_3$ | CH$_3$ | 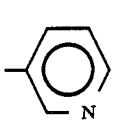 | 14.4 |
| 14 | CF$_3$ | CH$_3$ | 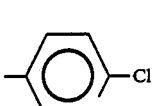 | 29.5 |
| 15 | CF$_3$ | CH$_3$ | 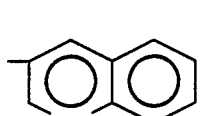 | 7.4 |
| 16 | Cl | CH$_3$ | 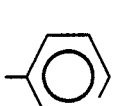 | 6.8 |
| 17 | NO$_2$ | CH$_3$ | 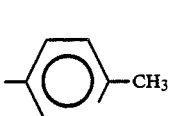 | 15.5 |
| 18 | NO$_2$ | CH$_3$ | 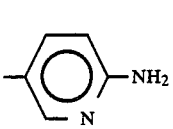 | 1.9 |
| 19 | NO$_2$ | CH$_3$ | 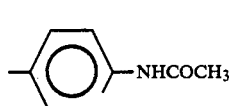 | 1.4 |
| 20 | NO$_2$ | CH$_3$ | 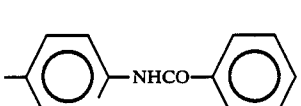 | 2.0 |

TABLE 5-continued
| Example | R₂ | R₄ | R₁ | Specific potency |
|---|---|---|---|---|
| 21 | NO₂ | CH₃ | 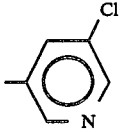 3-chloropyridin-5-yl | 16.7 |
| 22 | CF₃ | CH₃ | 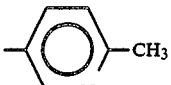 2-methylpyridin-5-yl | 9.2 |
| 23 | CF₃ | (CH₂)₂OCH₃ | 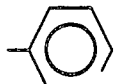 pyridin-3-yl | 135.4 |
| 24 | NO₂ | CH₃ | 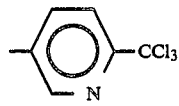 2-trichloromethylpyridin-5-yl | 3.1 |
| 25 | NO₂ | CH₃ |  2-iodopyridin-5-yl | 17.1 |
| 26 | NO₂ | CH₃ | 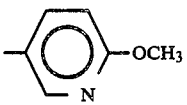 2-methoxypyridin-5-yl | 5.9 |
| 27 | NO₂ | CH₃ | 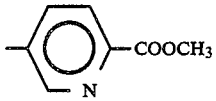 2-methoxycarbonylpyridin-5-yl | 4.6 |
| 28 | NO₂ | CH₃ | 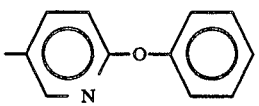 2-phenoxypyridin-5-yl | 3.6 |
| 29 | NO₂ | C₂H₅ | 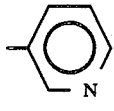 pyridin-3-yl | 31.0 |
| 30 | NO₂ | i-C₃H₇ | 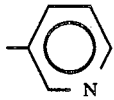 pyridin-3-yl | 130.0 |
| 31 | NO₂ | i-C₄H₉ | 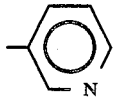 pyridin-3-yl | 103.2 |
| 32 | NO₂ | (CH₂)₂OCH₃ | 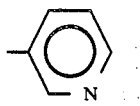 pyridin-3-yl | 5.9 |

TABLE 5-continued

| Example | R₂ | R₄ | R₁ | Specific potency |
|---|---|---|---|---|
| 33 | CF₃ | CH₃ | 5-methyl-2-methoxypyridinyl | 12.3 |
| 34 | CF₃ | i-C₄H₉ | pyridinyl | 8.2 |
| 35 | CF₃ | i-C₄H₉ | quinolinyl | 8.0 |
| 36 | CF₃ | i-C₄H₉ | 8-methylquinolinyl | 17.6 |
| 37 | NO₂ | (CH₂)₂OCH₃ | quinolinyl | 135.4 |
| 38 | CF₃ | (CH₂)₂OCH₃ | quinolinyl | 26.0 |
| 39 | NO₂ | CH₃ | 6-methoxyquinolinyl | 10.3 |
| 40 | NO₂ | CH₃ | 8-methylquinolinyl | 5.4 |
| 41 | NO₂ | i-C₄H₉ | quinolinyl | 15.9 |
| 42 | CF₃ | i-C₄H₉ | 6-methoxyquinolinyl | 3.8 |
| 43 | CF₃ | CH₃ | 6-methoxyquinolinyl | 2.1 |
| 44 | CF₃ | CH₃ | 8-methylquinolinyl | 9.0 |

TABLE 5-continued

| Example | R2 | R4 | R1 | Specific potency |
|---|---|---|---|---|
| 45 | NO2 | i-C3H7 | 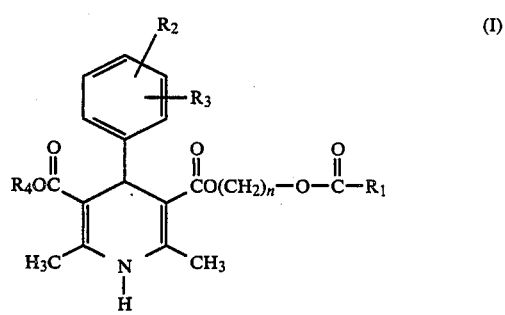 (quinoline with OCH3) | 10.8 |
| 46 | NO2 | CH3 | (pyridine with Cl) | 9.4 |

Remarks:
R3 is Cl in Example 16, but R3 is H in other examples.

EXAMPLE 47

A syrup containing 0.5% (weight per volume) of active ingredient was prepared from the following ingredients:

| | |
|---|---|
| Active ingredient | 0.5 g |
| D-sorbitol 70 W/V % | 25 g |
| Sugar | 30 g |
| Methyl p-oxybenzoate | 0.03 g |
| Glycerine | 0.15 g |
| Propyl p-oxybenzoate | 0.015 g |
| Flavouring agent | 0.2 g |
| 96% Ethanol | 0.5 g |
| Distilled water | ad 100.0 ml |

Sugar, d-sorbitol and the active ingredient were dissolved in 60 g of warm water. After cooling, glycerine and solution of flavouring agents dissolved in ethanol were added. To the mixture water was then added to 100 ml.

The above named active ingredient may be replaced by other therapeutically active ingredients of the invention.

EXAMPLE 48

An active ingredient (50 mg) was mixed with lactose (50 mg), potato starch (20 mg) and colloidal silicic acid (9.5 mg). The mixture was moistened with a 10% solution of gelatine and was granulated through a 12-mesh sieve. After drying potato starch (10 mg), talc (0.75 mg) and magnesium stearate (0.75 mg) were admixed and the mixture thus obtained was pressed into tablets, each containing 50 mg of active ingredient. These tablets are coated with a 10% alcoholic solution of shellac and thereupon with an aqueous solution containing saccharose (45%), gum arabicum (5%), gelatine (4%) and dyestuff (0.2%). After the first five coatings talc and powdered sugar were used for powdering. The priming coat was then coated with a 66% sugar syrup and polished with a 10% carnauba wax solution in carbon tetrachloride.

EXAMPLE 49

Granules were prepared from active ingredient (50 mg), lactose (250 mg), potato starch (150 mg) and an alcoholic solution of polyvinylpyrrolidone (50 mg). After the drying step the granules were sieved through a 12×60 mesh sieve to prepare granules, each containing 50 mg of active ingredient.

What is claimed is:

1. A compound of formula I (structure: dihydropyridine with $R_2$, $R_3$ on phenyl; $R_4OC(O)$ and $CO(CH_2)_n-O-C(O)-R_1$ substituents; $H_3C$ and $CH_3$ on pyridine N-H)

wherein

R1 represents a furyl or thienyl group; a 6-membered unsaturated heterocyclic group having one nitrogen atom in in the ring said unsaturated heterocyclic group being optionally substituted at a carbon atom by one or more substituents selected from the group consisting of halogen atom, $CH_{3-x}Cl_x(x=1$ to 3), amino, acetylamino, benzoylamino, lower alkoxy, phenoxy, lower alkoxy carbonyl or lower alkyl and further said unsaturated heterocyclic optionally being fused with a benzene ring or a benzene ring substituted with a lower alkyl or lower alkoxy group; or a 6-membered unsaturated heterocyclic group having two nitrogen atoms in the ring;

R2 and R3 both represent halogen atoms, or one of R2 and R3 represents a nitro or trifluoromethyl group and the other represents a hydrogen atom;

R4 represents an alkyl group of 1-6 carbon atoms, an alkoxyalkyl group in which the alkyl portion has 1-6 carbon atoms and the alkoxy portion has 1-2 carbon atoms, or an ethoxyethoxymethyl group; and n represents 2 or 3; or pharmaceutically acceptable acid addition salts thereof.

2. A compound of claim 1 wherein R1 is selected from the group consisting of 2-furyl, 3-furyl, 2-thienyl and 3-thienyl.

3. A compound of claim 1 which is selected from the group consisting of (1) 2,6-dimethyl-4-(2-nitrophenyl)-1,4-dihydropyridine-3,5-dicarboxylic acid 3-(2-nicotinoyloxyethyl)ester-5-methyl ester;

(2) 2,6-dimethyl-4-(3-nitrophenyl)-1,4-dihydropyrine-3,5-dicarboxylic acid 3-(2-nicotinoyloxyethyl)ester-5-methyl ester;

(3) 2,6-dimethyl-4-(3-nitrophenyl)-1,4-dihydropyridine-3,5-dicarboxylic acid 3-(2-picolinoyloxyethyl)ester-5-methyl ester;

(4) 2,6-dimethyl-4-(3-nitrophenyl)-1,4-dihydropyridine-3,5-dicarboxylic acid 3-(2-isonicotinoyloxyethyl)ester-5-methyl ester (5) 2,6-dimethyl-4-(3-nitrophenyl)-1,4-dihydropyridine-3,5-dicarboxylic acid 3-[2-(2-chloronicotinoyloxy)ethyl]ester-5-methyl ester;

(6) 2,6-dimethyl-4-(3-nitrophenyl)-1,4-dihydropyridine-3,5-dicarboxylic acid 3-(2-pyrazinoyloxyethyl)ester-5-methyl ester;

(7) 2,6-dimethyl-4-(3-nitrophenyl)-1,4-dihydropyridine-3,5-dicarboxylic acid 3-[2-(3-quinolylcarbonyloxy)ethyl]ester-5-methyl ester;

(8) 2,6-dimethyl-4-(2-nintrophenyl)-1,4-dihydropyridine-3,5-dicarboxylic acid 3-(3-nicotinoyloxypropyl(ester-5-methyl ester;

(9) 2,6-dimethyl-4-(2-nitrphenyl)-1,4-dihydropyridine-3,5-dicarboxylic acid 3-[2-(3-thienylcarbonyloxy)ethyl]ester-5-methyl ester;

(10) 2,6-dimethyl-4-(2-nitrophenyl)-1,4-dihydropyridine-3,5-dicarboxylic acid 3-[2-(3-furylcarbonyloxyethyl]ester-5-methyl ester;

(11) 2,6-dimethyl-4-(2-nitrophenyl)-1,4-dihydropyridine-3,5-dicarboxylic acid 3-[2-(6-chloronicotinoyloxy)ethyl]-ester-5-methyl ester;

(12) 2,6-dimethyl-4-(2-nitrophenyl)-1,4-dihydropyridine-3,5-dicarboxylic acid 3-[2-(3-quinolylcarbonyloxy)ethyl]-ester-5-methyl ester;

(13) 2,6-dimethyl-4-(2-trifluoromethylphenyl)-1,4-dihydropyridine-3,5-dicarboxylic acid 3-(2-nicotinoyloxyethyl)ester-5-methyl ester;

(14) 2,6-dimethyl-4-(2-trifluoromethylphenyl)-1,4-dihydropyridine-3,5-dicarboxylic acid 3-[2-(6-chloronicotinoyloxy)ethyl]ester-5-methyl ester;

(15) 2,6-dimethyl-4-(2-trifluoromethylphenyl)-1,4-dihydropyridine-3,5-dicarboxylic acid 3-[2-(3-quinolylcarbonyloxy)ethyl]ester-5-methyl ester;

(16) 2,6-dimethyl-4-(2,3-dichlorophenyl)-1,4-dihydropyridine-3,5-dicarboxylic acid 3-(2-nicotinoyloxyethyl)ester-5-methyl ester;

(17) 2,6-dimethyl-4-(2-nitrophenyl)-1,4-dihydropyridine-3,5-dicarboxylic acid 3-[2-(6-methyl-nicotinoyloxy(ethyl)-ester-5-methyl ester;

(18) 2,6-dimethyl-4-(2-nitrophenyl)-1,4-dihydropyridine-3,5-dicarboxylic acid 3-[2-(6-aminonicotinoyloxy)ethyl]-ester-5-methyl ester;

(19) 2,6-dimethyl-4-(2-nitrophenyl)-1,4-dihydropyridine-3,5-dicarboxylic acid 3-[2-(6-acetamidonicotinoyloxy)-ethyl]ester-5-methyl ester;

(20) 2,6-dimethyl-4-(2-nitrophenyl)-1,4-dihydropyridine-3,5-dicarboxylic acid 3-[2-(6-benzamidonicotinoyloxy)-ethyl]ester-5-methyl ester;

(21) 2,6-dimethyl-4-(2-nitrophenyl)-1,4-dihydropyridine-3,5-dicarboxylic acid 3-[2-(5-chloronicotinoyloxy)ethyl]-ester-5-methyl ester;

(22) 2,6-dimethyl-4-(2-trifluoromethylphenyl)-1,4-dihydropyridine-3,5-dicarboxylic acid 3-[2-(6-methyl-nicotinoyloxy)ethyl]ester-5-methyl ester;

(23) 2,6-dimethyl-4-(2-trifluoromethylphenyl)-1,4-dihydropyridine-3,5-dicarboxylic acid 3-(2-nicotinoyloxyethyl)-ester-5-methoxyethyl ester;

(24) 2,6-dimethyl-4-(2-nitrophenyl)-1,4-dihydropyridine-3,5-dicarboxylic acid 3-[2-(6-trichloromethyl-nicotinoyloxy)ethyl]ester-5-methyl ester;

(25) 2,6-dimethyl-4-(2-nitrophenyl)-1,4-dihyropyridine-3,5-dicarboxylic acid 3-[2-(6-iodonicotinoyloxy)ethyl]-ester-5-methyl ester;

(26) 2,6-dimethyl-4-(2-nitrophenyl)-1,4-dihydropyridine-3,5-dicarboxylic acid 3-[2-(6-methoxynicotinoyloxy)ethyl]-ester-5-methyl ester;

(27) 2,6-dimethyl-4-(2-nitrophenyl)-1,4-dihydropyridine-3,5-dicarboxylic acid 3-[2-(6-methoxycarbonylnicotinoyloxy)ethyl]ester-5-methyl ester;

(28) 2,6-dimethyl-4-(2-nitrophenyl)-1,4-dihydropyridine-3,5-dicarboxylic acid 3-[2-(6-phenoxynicotinoyloxy)ethyl]ester-5-methyl ester;

(29) 2,6-dimethyl-4-(2-nitrophenyl)-1,4-dihydropyridine-3,5-dicarboxylic acid 3-(2-nicotinoyloxyethyl(ester-5-ethyl ester;

(30) 2,6-dimethyl-4-(2-nitrophenyl)-1,4-dihydropyridine-3,5-dicarboxylic acid 3-(2-nicotinoyloxyethyl(ester-5-isopropyl ester;

(31) 2,6-dimethyl-4-(2-nitrophenyl)-1,4-dihydropyridine-3,5-dicarboxylic acid 3-(2-nicotinoyloxyethyl)ester-5-isobutyl ester;

(32) 2,6-dimethyl-4-(2-nitrophenyl)-1,4-dihydropyridine-3,5-dicarboxylic acid 3-(2-nicotinoyloxyethyl)ester-5-methoxyethyl ester;

(33) 2,6-dimethyl-4-(2-trifluoromethylphenyl)-1,4-dihydropyridine-3,5-dicarboxylic acid 3-[2-(6-methoxynicotinoyloxy)ethyl-5-methyl ester;

(34) 2,6-dimethyl-4-(2-trifluoromethylphenyl)-1,4-dihydropyridine-3,5-dicarboxylic acid 3-(2-nicotinoyloxyethyl)ester-5-isobutyl ester;

(35) 2,6-dimethyl-4-(2-trifluoromethylphenyl)-1,4-dihydropyridine-3,5-dicarboxylic 3-[2-(3-quinolylcarbonyloxy)ethyl]ester-5-isobutyl ester;

(36) 2,6-dimethyl-4-(2-trifluoromethylphenyl)-1,4-dihydropyridine-3,5-dicarboxylic acid 3-[2-(8-methyl-3-quinolycarbonyloxy)ethyl]ester-5-isobutyl ester;

(37) 2,6-dimethyl-4-(2-nitrophenyl)-1,4-dihydropyridine-3,5-dicarboxylic acid 3-[2-(3-quinolylcarbonyloxy)ethyl]ester-5-methoxyethyl ester;

(38) 2,6-dimethyl-4-(2-trifluoromethylphenyl)-1,4-dihydropyridine-3,5-dicarboxylic acid 3-[2-(3-quinolylcarbonyloxy)ethyl]ester-5-methoxyethyl ester;

(39) 2,6-dimethyl-4-(2-nitrophenyl)-1,4-dihydropyridine-3,5-dicarboxylic acid 3-[2-(6-methoxy-3-quinolylcarbonyloxy)ethyl]ester-5-methyl ester;

(40) 2,6-dimethyl-4-(2-nitrophenyl)-1,4-dihydropyridine-3,5-dicarboxylic acid 3-[2-(8-methyl-3-quinolylcarbonyloxy)ethyl]ester-5-methyl ester;

(41) 2,6-dimethyl-4-(2-nitrophenyl)-1,4-dihydropyridine-3,5-dicarboxylic acid 3-[2-(3-quinolylcarbonyloxy)ethyl]ester-5-isobutyl ester;

(42) 2,6-dimethyl-4-(2-trifluoromethylphenyl)-1,4-dihydropyridine-3,5-dicarboxylic acid 3-[2-(6-methoxy-3-quinolylcarbonyloxy)ethyl]ester-5-isobutyl ester;

(43) 2,6-dimethyl-4-(2-trifluoromethylphenyl)-1,4-dihydropyridine-3,5-dicarboxylic acid 3-[2-(6-methoxy-3-quinolylcarbonyloxy)ethyl]ester-5-methyl ester;

(44) 2,6-dimethyl-4-(2-trifluoromethylphenyl)-1,4-dihydropyridine-3,5-dicarboxylic acid 3-[2-(8-methyl-3-quinolylcarbonyloxy)ethyl]ester-5-methyl ester;

(45) 2,6-dimethyl-4-(2-nitrophenyl(-,4-dihydropyridine-3,5-dicarboxylic acid 3-[2-(6-methoxy-3-quinolylcarbonyloxy)ethyl]ester-5-isopropyl ester; and

(46) 2,6-dimethyl-4-(2-nitrophenyl)-1,4-dihydroxypyridine-3,5-dicarboxylic acid 3-[2-(4-chloronicotinoyloxy)ethyl]-ester-5-methyl ester.

4. A compound of claim 1 wherein $R_1$ is 2-pyridyl, 3-pyridyl, 4-pyridyl, 2-pyrimidyl, 4-pyrimidyl, 5-pyrimidyl, 2-pyrazinyl, 3-pyridazinyl, 4-pyridazinyl, 2-quinolyl, 3-quinolyl, 4-quinolyl, 1-isoquinolyl, 3-isoquinolyl or 4-isoquinolyl.

5. A compound of claim 1 wherein $R_1$ is a 2-pyridyl, 3-pyridyl or 4-pyridyl group, which is substituted at a carbon atom by one or more radicals selected from the group consisting of halogen, $CCl_3$, amino, acetylamino, benzoylamino, lower alkoxy, phenoxy, lower alkoxy carbonyl and lower alkyl.

6. A compound of claim 1 wherein $R_1$ is 2-quinolyl, 3-quinolyl, 4-quinolyl, 1-isoquinolyl, 3-isoquinolyl or 4-isoquinolyl, the benzene ring of which is substituted by lower alkyl or lower alkoxy.

7. A compound of claim 1, 3 or 4 wherein one of $R_2$ and $R_3$ represents a trifluoromethyl group and the other represents a hydrogen atom; and $R_4$ is selected from the group consisting of methyl, ethyl, n-propyl, i-propyl, n-butyl, i-butyl, sec.-butyl, tert-butyl, methoxyethyl, ethoxyethyl and ethoxyethoxymethyl.

8. A compound of claim 1, 3 or 4 wherein $R_2$ and $R_3$ both represent halogen atoms; and $R_4$ is selected from the group consisting of methyl, ethyl, n-propyl, i-propyl, n-butyl, i-butyl, sec.-butyl, tert-butyl, methoxyethyl, ethoxyethyl and ethoxyethoxymethyl.

9. A compound of claim 1 wherein $R_2$ is at the 2-position and represents a nitro group.

10. A compound of claim 1 wherein $R_2$ is at the 2-position and represents a trifluoromethyl group.

11. A compound of claim 1 wherein $R_2$ is at the 2-position and $R_3$ is at the 3-position.

12. A pharmaceutical composition for treatment of cardiovascular diseases comprising an effective amount of a compound of claim 1, or a pharmaceutically acceptable addition salt thereof and a pharmaceutically acceptable inert carrier.

13. A pharmaceutical composition for treatment of cardiovascular diseases which coprises an effective amount of a compound of claim 3, of the acid addition salt thereof, and a pharmaceutically acceptable inert carrier.

* * * * *

UNITED STATES PATENT AND TRADEMARK OFFICE
CERTIFICATE OF CORRECTION

PATENT NO. : 4,757,071
DATED : July 12, 1988
INVENTOR(S) : Hiroyasu Koyama et al It is certified that error appears in the above-identified patent and that said Letters Patent is hereby corrected as shown below:

Col. 36, in compound (2), line 66, "1,4-hydropyrine-" should read --1,4-dihydropyridine--;

Col. 37, in compound (8), line 18, "propyl(ester" should read --propyl)ester--;

in compound (9), line 19, "(2-nitrphenyl)" should read --(2-nitrophenyl)--;

in compound (17), line 45, "nicotinoyloxy(ethyl]" should read "nicotinoyloxy)ethyl]--;

in compound (19), line 51, "acetamido" should read --acetylamino--;

UNITED STATES PATENT AND TRADEMARK OFFICE
CERTIFICATE OF CORRECTION

PATENT NO. : 4,757,071
DATED : July 12, 1988
INVENTOR(S) : Hiroyasu Koyama et al It is certified that error appears in the above-identified patent and that said Letters Patent is hereby corrected as shown below:

in compound (20), line 54 "zamidonictinoyloxy" should read --zoylaminonictinoyloxy--;

Col. 38, in compound (33), line 27, "ethyl-5-" should read --ethyl]-ester-5--;

in compound (45), line 61, "nitrophenyl (-2,4-" should read --nitrophenyl)-1,4- --.

Signed and Sealed this

Tenth Day of January, 1989

Attest:

DONALD J. QUIGG

Attesting Officer

Commissioner of Patents and Trademarks